(12) United States Patent
Beckett et al.

(10) Patent No.: US 7,173,053 B2
(45) Date of Patent: Feb. 6, 2007

(54) N-FORMYL HYDROXYLAMINE DERIVATIVES AS INHIBITORS OF BACTERIAL POLYPEPTIDE FORMYLASE FOR TREATING MICROBIAL INFECTIONS

(75) Inventors: Paul Raymond Beckett, Oxford (GB); Steven Launchbury, Oxford (GB); Gilles Pain, Oxford (GB); Lisa Marie Pratt, Oxford (GB)

(73) Assignee: British Biotech Pharmaceuticals Limited (GB)

( * ) Notice: Subject to any disclaimer, the term of this patent is extended or adjusted under 35 U.S.C. 154(b) by 393 days.

(21) Appl. No.: 10/432,252

(22) PCT Filed: Nov. 8, 2001

(86) PCT No.: PCT/GB01/04965

§ 371 (c)(1),
(2), (4) Date: Nov. 10, 2003

(87) PCT Pub. No.: WO02/41886

PCT Pub. Date: May 30, 2002

(65) Prior Publication Data

US 2004/0106666 A1    Jun. 3, 2004

(30) Foreign Application Priority Data

Nov. 23, 2000 (GB) .................. 0028519.7
Jul. 11, 2001 (GB) .................. 0116864.0

(51) Int. Cl.
*A61K 31/4164* (2006.01)
*C07D 235/04* (2006.01)

(52) U.S. Cl. ................ 514/394; 548/300.1; 548/302.7; 548/309.7; 548/310.1; 514/393

(58) Field of Classification Search ............ 548/300.1, 548/309.7, 310.1, 310.4; 514/393, 394
See application file for complete search history.

(56) References Cited

U.S. PATENT DOCUMENTS 5,665,753 A * 9/1997 Frazee et al. ................ 514/394
5,703,092 A * 12/1997 Xue et al. .................... 514/303
5,733,882 A * 3/1998 Carr et al. ..................... 514/19

FOREIGN PATENT DOCUMENTS

| WO | WO 95 23790 | 9/1995 |
| WO | WO 96 33176 | 10/1996 |
| WO | WO 99 39704 | 8/1999 |
| WO | WO 99 59568 | 11/1999 |
| WO | WO 00 61134 | 10/2000 |

OTHER PUBLICATIONS

Chen et al.: "Design, synthesis, activity, and structure of a novel class of matrix metalloproteinase inhibitors containing a heterocyclic P2'-P3' amide bond isostere"; Bioorganic & Medicinal Chemistry Letters; vol. 6, No. 13, Jul. 9, 1996; pp. 1601-1606; XP004175762.

* cited by examiner

Primary Examiner—Golam M. M. Shameem
(74) Attorney, Agent, or Firm—Banner & Witcoff, Ltd.

(57) ABSTRACT

Compounds of formula (I) are antibacterial or antiprotozoal agents for treatment of infections in humans and non-human mammals, wherein: Z represents a radical of formula —N(OH)CH(=O) or formula C(=O)NH(OH); $R_1$ represents hydrogen, methyl or trifluromethyl, or except when Z is a radical of formula —N(OH)(=O), a hydroxy, halo or amino group; $R_2$ represents a group $R_{10}$—$(X)_n$-$(ALK)_m$— wherein $R_{10}$, ALK, X, m and n are as defined in the specification; $R^3$ represents hydrogen, $(C_1$–$C_6)$ alkyl or phenyl$(C_1$–$C_6)$alkyl-; and $R_5$ and $R_6$ are as defined in the specification.

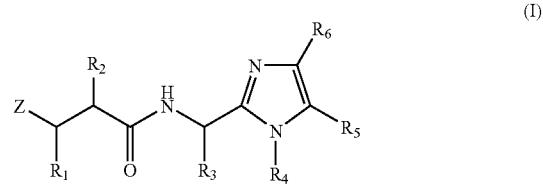

(I)

8 Claims, No Drawings

N-FORMYL HYDROXYLAMINE DERIVATIVES AS INHIBITORS OF BACTERIAL POLYPEPTIDE FORMYLASE FOR TREATING MICROBIAL INFECTIONS

This application is a National Stage application of co-pending PCT application PCT/GB01/04965 filed Nov. 8, 2001, which was published in English under PCT Article 21(2) on May 30, 2002, which claims the benefit of GB patent applications Serial No(s). 0028519.7 filed Nov. 2, 2000 and 0116864.0 filed Jul. 11, 2001. These applications are incorporated herein by reference in their entireties.

This invention relates to the use of hydroxamic acid and N-formyl hydroxylamine derivatives as antibacterial and antiprotozoal agents, to novel compounds within those classes, and to pharmaceutical and veterinary compositions comprising such compounds.

BACKGROUND TO THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as Staphylococci, Streptococci, Mycobacteria and Enterococci, resistant strains have evolved/arisen which makes them particularly difficult to eradicate. Examples of such strains are methicillin resistant *Staphylococcus aureus* (MRSA), methicillin resistant coagulase negative *Staphylococci* (MRCNS), penicillin, quinolone or macrolide resistant *Streptococcus pneumoniae* and multiply resistant *Enterococcus faecium*.

Pathogenic bacteria are often resistant to the aminoglycoside, β-lactam (penicillins and cephalosporins), macrolide, quinolone and chloramphenicol types of antibiotic. The mechanism of resistance can involve the enzymatic inactivation of the antibiotic by hydrolysis, formation of inactive derivatives, mutation of the molecular target and/or activation of transport pumps. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849–62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidoglycan precursor. The high-level resistance to vancomycin is known as VanA and is conferred by genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant enterococci and β-lactam antibiotic-resistant bacteria, such as methicillin-resistant *Staphylococcus aureus*, is of utmost importance.

BRIEF DESCRIPTION OF THE INVENTION

This invention is based on the finding that certain hydroxamic acid and N-formyl hydroxylamine derivatives having imidazole substituents have antibacterial and antiprotozoal activity, and makes available new antibacterial and antiprotozoal agents. The compounds with which this invention is concerned are antibacterial with respect to a range of Gram-positive and Gram-negative organisms.

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

All ribosome-mediated synthesis of proteins starts with a methionine residue. In prokaryotes, the methionyl moiety carried by the initiator tRNA is N-formylated prior to its incorporation into a polypeptide. Consequently, N-formyl-methionine is always present at the N-terminus of a nascent bacterial polypeptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290:607–614, 1999). Deformylation is, therefore, a crucial step in bacterial protein biosynthesis and the enzyme responsible, PDF, is essential for normal bacterial growth. Although the gene encoding PDF (def) is present in all pathogenic bacteria for which sequences are known (Meinnel et al., J. Mol. Biol, 266:939–49, 1997), it has no known eukaryotic counterpart, making it an attractive target for antibacterial chemotherapy (for a review see Giglione et al., Mol Microbiol., 36: 1197–1205, 2000).

The isolation and characterisation of PDF has been facilitated by an understanding of the importance of the metal ion in the active site (Groche et al., Biophys. Biochem. Res. Commun., 246:324–6, 1998). The $Fe^{2+}$ form is highly active in vivo but is unstable when isolated due to oxidative degradation (Rajagopalan et al., J. Biol. Chem. 273:22305–10, 1998). The $Ni^{2+}$ form of the enzyme has specific activity comparable with the ferrous enzyme but is oxygen-insensitive (Ragusa et al., J. Mol. Biol. 1998, 280: 515–23, 1998). The $Zn^{2+}$ enzyme is also stable but is almost devoid of catalytic activity (Rajagopalan et al., J. Am. Chem. Soc. 119:12418–12419, 1997).

Several X-ray crystal structures and NMR structures of *E. coli* PDF, with or without bound inhibitors, have been published (Chan et al., Biochemistry 36:13904–9, 1997; Becker et al., Nature Struct. Biol. 5:1053–8, 1998; Becker et al., J. Biol. Chem. 273:11413–6, 1998; Hao et al., Biochemistry, 38:4712–9, 1999; Dardel et al., J. Mol. Biol. 280:

501–13, 1998; O'Connell et al., J. Biomol. NMR, 13:311–24, 1999), indicating similarities in active site geometry to metalloproteinases such as thermolysin and the metzincins.

The substrate specificity of PDF has been extensively studied (Ragusa et al., J. Mol. Biol. 289:1445–57,1999; Hu et al., Biochemistry 38:643–50, 1999; Meinnel et al., Biochemistry, 38:4287–95, 1999). These authors conclude that an unbranched hydrophobic chain is preferred at P1', while a wide variety of P2' substituents are acceptable and an aromatic amide substituent may be advantageous at the P3' position. There have also been reports that small peptidic compounds containing an H-phosphonate (Hu et al., Bioorg. Med. Chem. Lett., 8:2479–82, 1998) or thiol (Meinnel et al., Biochemistry, 38:4287–95, 1999; Huntingdon et al., Biochemistry, 39: 4543–51, 2000; Wei et al, J. Combinatorial Chem., 2: 650–57, 2000) metal binding group are micromolar inhibitors of PDF. Peptide aldehydes such as calpeptin (N-Cbz-Leu-norleucinal) have also been shown to inhibit PDF (Durand et al., Arch. Biochem. Biophys., 367:297–302, 1999). Recently, the naturally occurring hydroxamic acid antibiotic actinonin, for which the target of its antibacterial activity was previously unknown, was shown to be a potent inhibitor of polypeptide deformylase (WO 99/39704, and Chen et al, Biochemistry, 39: 1256–62, 2000). Examples of non-peptidic PDF inhibitors with a carboxylic acid (Green et al., Arch. Biochem. Biophys. 375: 355–8, 2000; Jayasekera et al., ibid., 381:313–6, 2000) or hydroxamic acid (Apfel et al., J. Med. Chem., 43: 2324–31, 2000) metal binding groups are also known.

It has been reported that PDF is present in eukaryotic parasites such as *Plasmodium falciparum* (Meinnel, Parasitology Today, 16: 165–8, 2000). Those authors also found evidence for the presence of PDF in other parasites of humans, such as the kinetoplastid protozoan parasites *Trypanosoma brucei* and *Leishmania major*. Based on these findings, it is anticipated that the hydroxamic acid and N-formyl hydroxylamine compounds with which this invention is concerned have antiprotozoal activity, and are useful in the treatment of malaria and other protozoal diseases.

Certain N-formyl hydroxylamine derivatives have previously been claimed in the patent publications listed below, although very few examples of such compounds have been specifically made and described:

| | |
|---|---|
| EP-B-0236872 | (Roche) |
| WO 92/09563 | (Glycomed) |
| WO 92/04735 | (Syntex) |
| WO 95/19965 | (Glycomed) |
| WO 95/22966 | (Sanofi Winthrop) |
| WO 95/33709 | (Roche) |
| WO 96/23791 | (Syntex) |
| WO 96/16027 | (Syntex/Agouron) |
| WO 97/03783 | (British Biotech) |
| WO 97/18207 | (DuPont Merck) |
| WO 98/38179 | (Glaxo-Wellcome) |
| WO 98/47863 | (Labs Jaques Logeais) |
| WO 99/06361 | (Abbott Laboratories) |
| WO 00/12082 | (Glaxo-Wellcome) |
| WO 00/12083 | (Glaxo-Wellcome) |
| WO 00/12466 | (Glaxo-Wellcome) |
| WO 00/12478 | (Zeneca) |
| WO 00/44712 | (Abbott Laboratories) |
| WO 00/44739 | (Abbott Laboratories) |
| WO 00/59285 | (DuPont Pharmaceuticals) |

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis.

In addition to these, U.S. Pat. No. 4,738,803 (Roques et al.) also discloses N-formyl hydroxylamine derivatives, however, these compounds are disclosed as enkephalinase inhibitors and are proposed for use as antidepressants and hypotensive agents. Also, WO 97138705 (Bristol-Myers Squibb) and a recent publication (Robl et al., Bioorg. Med. Chem. Lett., 10: 257–60, 2000) disclose certain N-formyl hydroxylamine derivatives as enkephalinase and angiotensin converting enzyme inhibitors.

Patent publications WO 99/41232 (British Biotech) and WO 00/43001 (British Biotech) respectively disclose the use of certain N-formyl hydroxylamine derivatives as inhibitors of proliferation of rapidly dividing cells and in the treatment of inflammation.

Very many hydroxamic acid derivatives are known. Many have been disclosed as having matrix metalloproteinase (MMP) inhibitory activity, and thus to be potentially useful for the treatment of diseases mediated by MMPs, for example cancer, arthritides, and contitions involving tissue remodeling such as wound healing, and restenosis. WO 95/23790 (SmithKline Beecham) discloses MMP and cytokine inhibiting hydroxamic acid derivatives of formula (A)

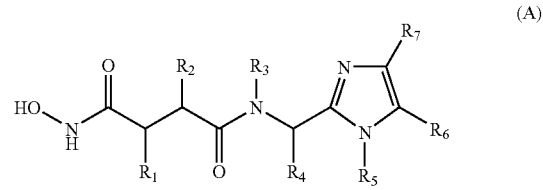

(A)

wherein the variable R groups are as defined in the specification. Similar compounds have been disclosed in WO 96/33176 (DuPont Merck) and in Chen et. al., Bioorg. Med. Chem. Lett., 1996, 6, 1601–1606, as inhibitors of MMPs and inhibitors of Tumour Necrosis Factor production. Neither of these publications suggest that compounds (A) have antibacterial or antiprotozoal activity.

Our copending International patent applications nos. WO 99/39704, WO 99/59568, WO 00/35440, WO 00/44373, WO 00/58294 and WO 00/61134 disclose that certain N-formyl hydroxylamine and hydroxamic acid derivatives have antibacterial activity.

DETAILED DESCRIPTION OF THE INVENTION

According to the first aspect of the present invention there is provided the use of a compound of formula (I) or a pharmaceutically or veterinarily acceptable salt, hydrate or solvate thereof in the preparation of a composition for treatment of bacterial or protozoal infections in humans and non-human mammals:

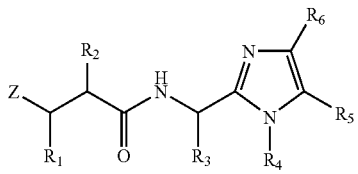

wherein:

Z represents a radical of formula —N(OH)CH(=O) or formula —C(=O)NH(OH);

$R_1$ represents hydrogen, methyl or trifluoromethyl, or, except when Z is a radical of formula —N(OH)CH(=O), a hydroxy, halo or amino group;

$R_2$ represents a group $R_{10}$—(X)$_n$-(ALK)$_m$— wherein $R_{10}$ represents hydrogen, or a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, halo (including fluoro, chloro, bromo and iodo), trifluoromethyl, cyano, nitro, oxo, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$–$C_6$)alkyl group and ALK represents a straight or branched divalent $C_1$–$C_6$ alkylene, $C_2$–$C_6$ alkenylene, or $C_2$–$C_6$ alkynylene radical, and may be interrupted by one or more non-adjacent —NH—, —O— or —S— linkages, X represents —NH—, —O— or —S—, and m and n are independently 0 or 1;

$R_3$ represents the side chain of a natural or non-natural alpha amino acid; and $R_4$ represents hydrogen, ($C_1$–$C_6$)alkyl or phenyl($C_1$–$C_6$)alkyl-; and (a) $R_5$ and $R_6$ independently represent:

hydrogen, halogen, trifluoromethyl, or ($C_1$–$C_6$)alkyl, ($C_2$–$C_6$)alkenyl, ($C_2$–$C_6$)alkynyl, aryl, heterocyclyl, aryl($C_1$–$C_6$)alkyl-, or heterocyclyl ($C_1$–$C_6$)alkyl-, any of which may be optionally substituted by ($C_1$–$C_6$)alkyl, halogen, trifluoromethyl, cyano, nitro, oxo, phenoxy or phenylthio-,
—OR$^A$, —SR$^A$, —NHR$^A$, —NR$^A$R$^B$, —NHCOR$^A$, —CONR$^A$R$^A$, —CONR$^A$R$^B$, or —COOR$^A$, wherein R$^A$ and R$^B$ are independently hydrogen or ($C_1$–$C_4$) alkyl, or in the case where R$^A$ and R$^B$ are attached to a nitrogen atom then R$^A$ and R$^B$ taken together with the nitrogen atom to which they are attached form a monocyclic 5–7 membered ring; or (b) $R_5$ and $R_6$ taken together with the carbon atoms to which they are attached form a fused monocyclic or bicyclic carbocyclic or heterocyclic ring which may be further substituted with any of the substituent groups listed under (a).

In another aspect, the invention provides a method for the treatment of bacterial or protozoal infections in humans and non-human mammals, which comprises administering to a subject suffering such infection an antibacterially or antiprotozoally effective dose of a compound of formula (I) as defined above.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

Compounds of formula (I) above wherein Z is a radical of formula —N(OH)CH(=O), are believed to be novel. Accordingly, in another aspect, the invention provides a compound of formula (I) wherein Z is a radical of formula —N(OH)CH(=O), or a pharmaceutically or veterinarily acceptable salt, hydrate or solvate thereof. Furthermore, to the extent that compounds of formula (I) above wherein Z is a radical of formula —C(=O)NH(OH) do not form part of the state of the art, such compounds and their pharmaceutically or veterinarily acceptable salts, hydrates or solvates are also an aspect of the present invention.

On the hypothesis that the compounds (I) act by inhibition of intracellular PDF, the most potent antibacterial effect may be achieved by using compounds which efficiently pass through the bacterial cell wall. Thus, compounds which are highly active as inhibitors of PDF in vitro and which penetrate bacterial cells are preferred for use in accordance with the invention. It is to be expected that the antibacterial potency of compounds which are potent inhibitors of the PDF enzyme in vitro, but are poorly cell penetrant, may be improved by their use in the form of a prodrug, ie a structurally modified analogue which is converted to the parent molecule of formula (I), for example by enzymic action, after it has passed through the bacterial cell wall. The same is true in the case of protozoa.

As used herein the term "($C_1$–$C_6$)alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent ($C_1$–$C_6$)alkylene radical" means a saturated hydrocarbon chain having from 1 to 6 carbon atoms and two unsatisfied valencies.

As used herein the term "($C_2$–$C_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent ($C_2$–$C_6$)alkenylene radical" means a hydrocarbon chain having from 2 to 6 carbon atoms, at least one double bond, and two unsatisfied valencies.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_2$–$C_6$)alkynylene radical" means a hydrocarbon chain having from 2 to 6 carbon atoms, at least one triple bond, and two unsatisfied valencies.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the unqualified term "heterocyclyl" or "heterocyclic" includes "heteroaryl" as defined below, and in particular means a 5–8 membered aromatic or non-aromatic heterocyclic ring containing one or more heteroatoms selected from S, N and O, and optionally fused to a benzyl or second heterocyclic ring, and the term includes, for example, pyrrolyl, furyl, thienyl, piperidinyl, imidazolyl, oxazolyl, thiazolyl, thiadiazolyl, thiazepinyl, pyrazolyl, pyridinyl, pyrrolidinyl, pyrimidinyl, morpholinyl, piperazinyl, indolyl, and benzimidazolyl rings.

As used herein the term "heteroaryl" refers to a 5- or 6-membered aromatic ring containing one or more heteroatoms, and optionally fused to a benzyl or pyridyl ring; and to groups consisting of two covalently linked 5- or 6-membered aromatic rings each containing one or more heteroatoms; and to groups consisting of a monocyclic carbocyclic aromatic group covalently linked to a 5- or 6-membered aromatic rings containing one or more heteroatoms. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the unqualified term "carbocyclyl" or "carbocyclic" refers to a 5–8 membered ring whose ring atoms are all carbon.

Unless otherwise specified in the context in which it occurs, the term "substituted" as applied to any moiety herein means substituted with up to four substituents, each of which independently may be $(C_1–C_6)$alkyl, phenyl, benzyl, $(C_1–C_6)$alkoxy, phenoxy, hydroxy, mercapto, $(C_1–C_6)$alkylthio, amino, halo (including fluoro, chloro, bromo and iodo), trifluoromethyl, cyano, nitro, oxo, —COOH, —CONH$_2$, —COR$^A$, —COOR$^A$, —NHCOR$^A$, —CONHR$^A$, —NHR$^A$, —NR$^A$R$^B$, or —CONR$^A$R$^B$ wherein R$^A$ and R$^B$ are independently a $(C_1–C_6)$alkyl group. In the case where "substituted" means substituted by benzyl, the phenyl ring thereof may itself be substituted with any of the foregoing, except phenyl or benzyl.

As used herein the terms "side chain of a natural alpha-amino acid" and "side chain of a non-natural alpha-amino acid" mean the group R$^x$ in respectively a natural and non-natural amino acid of formula NH$_2$—CH(R$^x$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example amino, carboxyl, hydroxy, mercapto, guanidyl, imidazolyl, or indolyl groups as in arginine, lysine, glutamic acid, aspartic acid, tryptophan, histidine, serine, threonine, tyrosine, and cysteine, such functional substituents may optionally be protected.

Likewise, in the side chains of non-natural alpha amino acids which contain functional substituents, for example amino, carboxyl, hydroxy, mercapto, guanidyl, imidazolyl, or indolyl groups, such functional substituents may optionally be protected.

The term "protected" when used in relation to a functional substituent in a side chain of a natural or non-natural alpha-amino acid means a derivative of such a substituent which is substantially non-functional. The widely used handbook by T. W. Greene and P. G. Wuts "Protective Groups in Organic Synthesis" Second Edition, Wiley, N.Y., 1991 reviews the subject. For example, carboxyl groups may be esterified (for example as a $C_1–C_6$ alkyl ester), amino groups may be converted to amides (for example as a NHCOC$_1$–C$_6$ alkyl amide) or carbamates (for example as an NHC(=O)OC$_1$–C$_6$ alkyl or NHC(=O)OCH$_2$Ph carbamate), hydroxyl groups may be converted to ethers (for example an OC$_1$–C$_6$ alkyl or a O(C$_1$–C$_6$ alkyl)phenyl ether) or esters (for example a OC(=O)C$_1$–C$_6$ alkyl ester) and thiol groups may be converted to thioethers (for example a tert-butyl or benzyl thioether) or thioesters (for example a SC(=O)C$_1$–C$_6$ alkyl thioester).

There are at least two actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the R$_2$ group is R; that of the carbon atom carrying the R$_1$ group (when asymmetric) is R; and that of the carbon atom carrying the R$_3$ group (when asymmetric) is S In the compounds of formula (I) as defined above:

When Z is a radical of formula —N(OH)CH(=O) R$_1$ is hydrogen, methyl or trifluoromethyl. When Z is a radical of formula —C(=O)NH(OH) R$_1$ is hydrogen, methyl, trifluoromethyl, hydroxy, halo (e.g. chloro, bromo or especially fluoro) or amino. Hydrogen is currently preferred in both cases.

R$_2$ may be, for example:

optionally substituted $C_1–C_8$ alkyl, $C_3–C_6$ alkenyl, $C_3–C_6$ alkynyl or cycloalkyl;

phenyl($C_1–C_6$ alkyl)-, phenyl($C_3–C_6$ alkenyl)- or phenyl ($C_3–C_6$ alkynyl)- optionally substituted in the phenyl ring;

cycloalkyl($C_1–C_6$ alkyl)-, cycloalkyl($C_3–C_6$ alkenyl)- or cycloalkyl($C_3–C_6$ alkynyl)- optionally substituted in the cycloalkyl ring;

heterocyclyl($C_1–C_6$ alkyl)-, heterocyclyl($C_3–C_6$ alkenyl)- or heterocyclyl($C_3–C_6$ alkynyl)- optionally substituted in the heterocyclyl ring; or CH$_3$(CH$_2$)$_p$O(CH$_2$)$_q$— or CH$_3$(CH$_2$)$_p$S(CH$_2$)$_q$—, wherein p is 0, 1, 2 or 3 and q is 1, 2 or 3.

Specific examples of R$_2$ groups include methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl) prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at $R_2$ are n-propyl, n-butyl, n-pentyl, and cyclopentylmethyl.

$R_3$ may be, for example the characterising group of a natural α-amino acid, for example benzyl, or 4-hydroxyphenylmethyl, in which any functional group may be protected, any amino group may be acylated and any carboxyl group present may be amidated; or a group $-[Alk]_nR_9$ where Alk is a $(C_1-C_6)$alkylene or $(C_2-C_6)$alkenylene group optionally interrupted by one or more —O—, or —S— atoms or —N($R_{12}$)— groups [where $R_{12}$ is a hydrogen atom or a $(C_1-C_6)$alkyl group], n is 0 or 1, and $R_9$ is hydrogen or an optionally substituted phenyl, aryl, heterocyclyl, cycloalkyl or cycloalkenyl group or (only when n is 1) $R_9$ may additionally be hydroxy, mercapto, $(C_1-C_6)$alkylthio, amino, halo, trifluoromethyl, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a $(C_1-C_6)$alkyl group; or a benzyl group substituted in the phenyl ring by a group of formula —OCH$_2$COR$_8$ where $R_8$ is hydroxyl, amino, $(C_1-C_6)$alkoxy, phenyl$(C_1-C_6)$alkoxy, $(C_1-C_6)$alkylamino, di$((C_1-C_6)$alkyl)amino, phenyl$(C_1-C_6)$alkylamino; or a heterocyclic$(C_1-C_6)$alkyl group, either being unsubstituted or mono- or di-substituted in the heterocyclic ring with halo, nitro, carboxy, $(C_1-C_6)$alkoxy, cyano, $(C_1-C_6)$alkanoyl, trifluoromethyl $(C_1-C_6)$alkyl, hydroxy, formyl, amino, $(C_1-C_6)$alkylamino, di-$(C_1-C_6)$alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl; or a group —CR$_a$R$_b$R$_c$ in which:
  each of $R_a$, $R_b$ and $R_c$ is independently hydrogen, $(C_1-C_6)$alkyl, $(C_2-C_6)$alkenyl, $(C_2-C_6)$alkynyl, phenyl$(C_1-C_6)$alkyl, $(C_3-C_8)$cycloalkyl; or
  $R_c$ is hydrogen and $R_a$ and $R_b$ are independently phenyl or heteroaryl such as pyridyl; or
  $R_c$ is hydrogen, $(C_1-C_6)$alkyl, $(C_2-C_6)$alkenyl, $(C_2-C_6)$alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or
  $R_a$, $R_b$ and $R_c$ together with the carbon atom to which they are attached form a tricyclic ring (for example adamantyl); or
  $R_a$ and $R_b$ are each independently $(C_1-C_6)$alkyl, $(C_2-C_6)$alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, $(C_1-C_4)$perfluoroalkyl, —CH$_2$OH, —CO$_2(C_1-C_6)$alkyl, —O$(C_1-C_6)$alkyl, —O$(C_2-C_6)$alkenyl, —S$(C_1-C_6)$alkyl, —SO$(C_1-C_6)$alkyl, —SO$_2(C_1-C_6)$ alkyl, —S$(C_2-C_6)$alkenyl, —SO$_2(C_2-C_6)$alkenyl, —SO$_2(C_2-C_6)$alkenyl or a group -Q-W wherein Q represents a bond or —O—, —S—, —SO— or —SO$_2$ and W represents a phenyl, phenylalkyl, $(C_3-C_8)$cycloalkyl, $(C_3-C_8)$cycloalkylalkyl, $(C_4-C_8)$cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —CO$_2$H, —CO$_2(C_1-C_6)$ alkyl, —CONH$_2$, —CONH$(C_1-C_6)$alkyl, —CONH$(C_1-C_6$alkyl)$_2$, —CHO, —CH$_2$OH, $(C_1-C_4)$perfluoroalkyl, —O$(C_1-C_6)$alkyl, —S$(C_1-C_6)$alkyl, —SO$(C_1-C_6)$alkyl, —SO$_2(C_1-C_6)$alkyl, —NO$_2$, —NH$_2$, —NH$(C_1-C_6)$alkyl, —N$((C_1-C_6)$alkyl)$_2$, —NHCO$(C_1-C_6)$alkyl, $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl or benzyl.

Examples of particular $R_3$ groups include methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxyethyl, 2-carboxyethyl, 2-methylcarbamoylethyl, 2-carbamoylethyl, and 4-aminobutyl. Presently preferred $R_3$ groups include tert-butyl.

$R_4$ may be, for example, hydrogen, methyl or ethyl.

$R_5$ and $R_6$ may independently be, for example, hydrogen, methyl, trifluoromethyl, phenyl, bromo, chloro, fluoro, methoxy, hydroxymethyl, dimethylaminomethyl-, ethoxymethyl-, 4-methyl-piperazine-1-carbonyl-, 4-methyl-piperazin-1-ylmethyl-, morpholin-4-ylmethyl-, methoxycarbonyl, thiazol-2-yl-, phenoxymethyl-, pyrrolidin-1-ylmethyl-, piperidin-1-ylmethyl-, —C(O)NH$_2$, (CH$_2)_2$CO$_2$CH$_3$, —CH(OH)CH(CH$_3)_2$, —CH(OH)CH$_3$, —CH(OH)Ph, or $R_5$ and $R_6$ taken together with the carbon atoms to which they are attached may form a fused benzo, naphtho or pyrido, for example a [4,5-c]pyridin-2-yl, ring, which may be substituted as specified, for example a fused benzo ring substituted by methyl, cyano, hydroxy, chloro or fluoro in the 4- or 5-position.

Specific examples of compounds within or for use within the scope of the invention include the following N-formyl hydroxylamine derivatives, and their corresponding hydroxamic acid analogues:

2R-Cyclopentylmethyl-N-[1S-(5-fluoro-1H-benzoimidazol-2-yl)-2,2-dimethyl-propyl]-3-(formyl-hydroxy-amino)-propionamide;

N-[1-(5-Chloro-1H-benzoimidazol-2-yl)-2,2-dimethyl-propyl]-2-cyclopentylmethyl-3-(formyl-hydroxy-amino)-propionamide;

N-[1-(1H-Benzoimidazol-2-yl)-2,2-dimethyl-propyl]-2-cyclopentylmethyl-3-(formyl-hydroxy-amino)-propionamide;

2-[(Formyl-hydroxy-amino)-methyl]-hexanoic acid [1-(1H-benzoimidazol-2-yl)-2,2-dimethyl-propyl]-amide;

3-Cyclopentyl-N-[1S-(6-dimethylaminomethyl-1H-benzoimidazol-2-yl)-2,2-dimethyl-propyl]-2R-[(formyl-hydroxy-amino)-methyl]-propionamide;

3-Cyclopentyl-N-[1S-(6-dimethylaminomethyl-1-methyl-1H-benzoimidazol-2-yl)-2,2-dimethyl-propyl]-2R-[(formyl-hydroxy-amino)-methyl]-propionamide;

N-(1S-{6-[(Acetyl-methyl-amino)-methyl]-1H-benzoimidazol-2-yl}-2,2-dimethyl-propyl)-3-cyclopentyl-2R-[(formyl-hydroxy-amino)-methyl]-propionamide;

3-Cyclopentyl-2R-[(formyl-hydroxy-amino)-methyl]-N-[1S-(6-hydroxymethyl-1H-benzoimidazol-2-yl)-2,2-dimethyl-propyl]-propionamide;

3-Cyclopentyl-N-[1S-(5-dimethylaminomethyl-1H-imidazol-2-yl)-2,2-dimethyl-propyl]-2R-[(formyl-hydroxy-amino)-methyl]-propionamide;

3-Cyclopentyl-N-[1S-(6-ethoxymethyl-1H-benzoimidazol-2-yl)-2,2-dimethyl-propyl]-2R-[(formyl-hydroxy-amino)-methyl]-propionamide;

3-Cyclopentyl-N-[1S-(5-ethoxymethyl-1H-imidazol-2-yl)-2,2-dimethyl-propyl]-2R-[(formyl-hydroxy-amino)-methyl]-propionamide;

N-[1S-(5{[(Benzo[1,3]dioxol-5-ylmethyl)-amino]-methyl}-1H-imidazol-2-yl)-2,2-dimethyl-propyl]-3-cyclopentyl-2R-[(formyl-hydroxy-amino)-methyl]-propionamide;

3-Cyclopentyl-2R-[(formyl-hydroxy-amino)-methyl]-N-[1S-(1H-imidazo[4,5-c]pyridin-2-yl)-2,2-dimethyl-propyl]-propionamide;

3-Cyclopentyl-N-[1S-(1-ethyl-1H-imidazo[4,5-c]pyridin-2-yl)-2,2-dimethyl-propyl]-2R-[(formyl-hydroxy-amino)-methyl]-propionamide;

3-Cyclopentyl-N-{2,2-dimethyl-1S-[5-(4-methyl-piperazine-1-carbonyl)-1H-imidazol-2-yl]-propyl}2R-[(formyl-hydroxy-amino)-methyl]-propionamide;

3-Cyclopentyl-N-{2,2-dimethyl-1S-[5-(4-methyl-piperazin-1-ylmethyl)-1H-imidazol-2-yl]-propyl}2R-[(formyl-hydroxy-amino)-methyl]-propionamide;

3-Cyclopentyl-N-[2,2-dimethyl-1S-(5-morpholin-4-ylmethyl-1H-imidazol-2-yl)-propyl]-2R-[(formyl-hydroxy-amino)-methyl]-propionamide;

3-Cyclopentyl-2R-[(formyl-hydroxy-amino)-methyl]-N-[1S-(1H-imidazol-2-yl)-2,2-dimethyl-propyl]-propionamide;

2-(1S-{3-Cyclopentyl-2R-[(formyl-hydroxy-amino)-methyl]-propionylamino}-2,2-dimethyl-propyl)-3H-imidazole-4-carboxylic acid methyl ester;

3-Cyclopentyl-N-[2,2-dimethyl-1S-(5-thiazol-2-yl-1H-imidazol-2-yl)-propyl]-2R-[(formyl-hydroxy-amino)-methyl]-propionamide;

3-Cyclopentyl-N-[2,2-dimethyl-1S-(5-phenoxymethyl-1H-imidazol-2-yl)-propyl]-2R-[(formyl-hydroxy-amino)-methyl]-propionamide;

3-Cyclopentyl-N-[2,2-dimethyl-1S-(5-pyrrolidin-1-ylmethyl-1H-imidazol-2-yl)-propyl]-2R-[(formyl-hydroxy-amino)-methyl]-propionamide; and 3-Cyclopentyl-N-[2,2-dimethyl-1S-(5-piperidin-1-ylmethyl-1H-imidazol-2-yl)-propyl]-2R-[(formyl-hydroxy-amino)-methyl]-propionamide.

Compounds of the invention wherein Z is a radical of formula —N(OH)CH(═O) may be prepared by deprotection of a compound of formula (II)

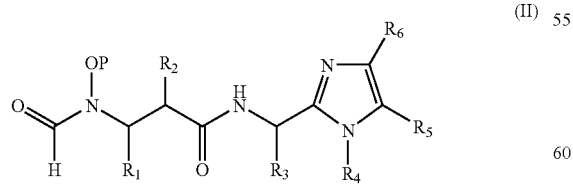

wherein P represents a hydroxy protecting group, and $R_1$, $R_2$, $R_3$, $R_4$, $R_5$ and $R_6$ are as defined in relation to formula (II). Compounds of formula (II) may be prepared by coupling a carboxylic acid of formula (III),

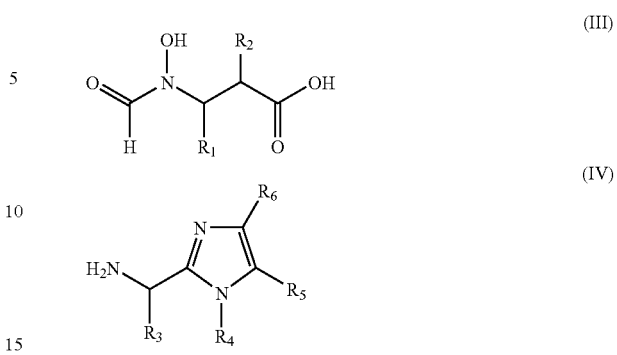

with an amine of formula (IV) using standard peptide coupling methods. Carboxylic acids of formula (III) may be prepared by analogy with the methods described in WO 99/39704. Amines of formula (IV) may be prepared according to any of a variety of methods described in the literature (Chen et al., Bioorg. Med. Chem. Lett., 1996, 6, 1601–1606; Gordon et al., Tetrahedron Lett. 34, 1901–1904, 1993; Gordon et al., Bioorg. Med. Chem. Lett., 1993, 3, 915–920; Abdel-Meguid et al., Biochemistry 33: 11671–7, 1994) and in (WO 93/02057, 95/23790 and WO 96/33176.

Hydroxamate compounds of formula (I) for use in accordance with the invention may be prepared by reacting a compound of formula (V) or a carboxyl-activated derivative thereof

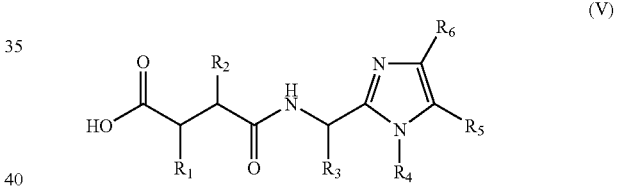

with hydroxylamine or an N- and/or O-protected hydroxylamine, and thereafter removing any O- or N-protecting groups. Carboxyl-activated derivatives of compound (V) include 1-hydroxybenzotriazole ester and pentafluorophenyl ester. A compound of formula (V) may be prepared by standard peptide coupling methods from a carboxylic acid of formula (VI), wherein P is as defined in relation to formula (II), and an amine of formula (IV), followed by removal of P.

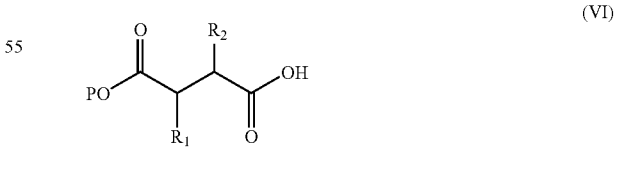

Compounds of formula (VI) are well known starting materials in the synthesis of matrix metalloproteinase inhibitors.

Antibacterial or antiprotozoal compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle. Intra-venous infusion is another route of administration for the compounds used in accordance with the invention.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate embodiments of the invention. $^1$H and spectra were recorded using a Bruker DPX 250 spectrometer at 250.1 MHz. Mass spectra were obtained using a Perkin Elmer Sciex API 165 spectrometer using both positive and negative ionisation modes. Analytical HPLC was performed on a Beckman System Gold, using Waters Nova Pak C18 column (150 mm, 3.9 mm) with 20 to 90% solvent B gradient (1 ml/min) as the mobile phase. [Solvent A: 0.05% TFA in 10% water 90% methanol; Solvent B: 0.05% TFA in 10% methanol 90%], detection wavelength at 214 nm. Preparative HPLC was performed on a Gilson autoprep instrument using a C18 Waters delta prep-pak cartridge (151 μm, 300 A, 25 mm, 10 mm) with 20 to 90% solvent B gradient (6 ml/min) as the mobile phase. [Solvent A water; Solvent B: methanol], UV detection was at 214 nm.

The following abbreviations have been used throughout:

| | |
|---|---|
| EDC | N-Ethyl-N'-(3-dimethylaminopropyl)carbodiimide hydrochloride |
| HPLC | High performance liquid chromatography |
| LRMS | Low resolution mass spectrometry |
| NMR | Nuclear magnetic resonance |
| RT | Retention Time |

EXAMPLE 1

2R-Cyclopentylmethyl-N-[1S-(5-fluoro-1H-benzoimidazol-2-yl)-2,2-dimethyl-propyl]-3-(formyl-hydroxy-amino)-propionamide

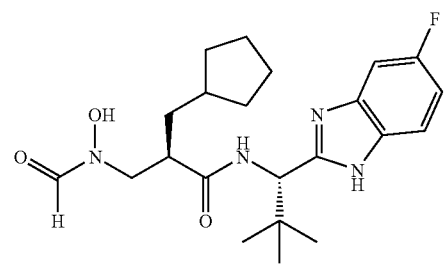

The title compound was prepared as outlined in Scheme 1 and is described in detail below.

Scheme 1

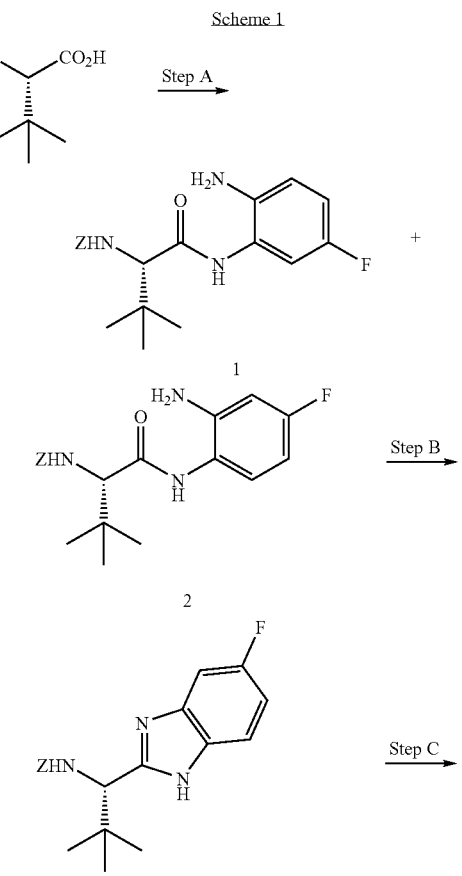

-continued

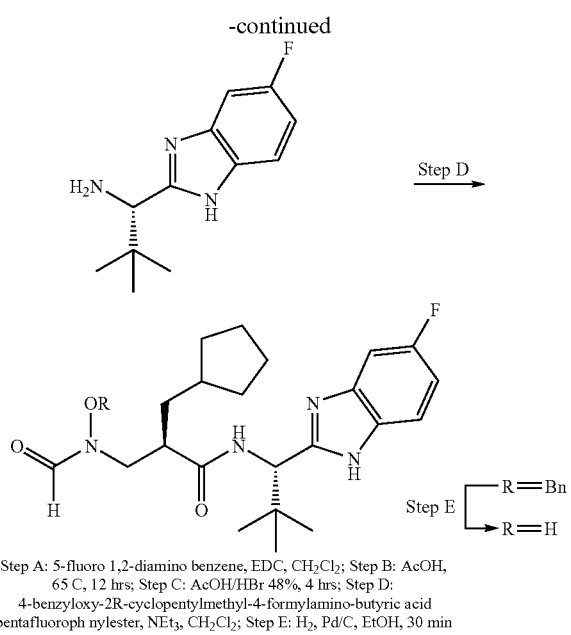

Step A: 5-fluoro 1,2-diamino benzene, EDC, CH₂Cl₂; Step B: AcOH, 65 C, 12 hrs; Step C: AcOH/HBr 48%, 4 hrs; Step D: 4-benzyloxy-2R-cyclopentylmethyl-4-formylamino-butyric acid pentafluoroph nylester, NEt₃, CH₂Cl₂; Step E: H₂, Pd/C, EtOH, 30 min Step A:

Compound 1: [1S-(2-Amino-5-fluoro-phenylcarbamoyl)-2,2-dimethyl-propyl]-carbamic acid benzyl ester Compound 2: [1S-(2-Amino-4-fluoro-phenylcarbamoyl)-2,2-dimethyl-propyl]-carbamic acid benzyl ester To a solution of Z-tert-leucine (4.04 g, 1.54 mmol) in dichloromethane (15 ml), was added the 1,2-diamine (2.57 g, 1.68 mmol) followed by EDC (3.21 g, 1.68 mmol). The resulting reaction mixture was stirred at room temperature for 12 hrs. The reaction mixture was then diluted with dichloromethane and washed with water (30 ml), 1M aq. Na₂CO₃ (30 ml), 1M HCl (20 ml) and brine. The combined organic layers were dried over anhydrous MgSO₄, filtered and the solvent was removed in vacuo to yield a pale yellow foam which was purified by flash chromatography (hexane:ethyl acetate, 3:1) to give a mixture of regioisomeric compounds, 1 and 2. A further purification by flash chromatography afforded compound 1 as a pure solid (2.44 g, 43% yield). ¹H-NMR; δ (CDCl₃, mixture of 1 and 2), 7.71 (1H, br s), 7.38–7.27 (5H, m), 7.04–6.98 (1H, m), 6.44–6.36 (2H, m), 5.63 (1H, br d), 5.13–4.99 (2H, AB system), 4.16–4.08 (1H, m), 3.94 (2H, br s), 1.09 (9H, s). (N.B. Both 1 and 2 give the same compound after cyclisation.)

Step B: [1S-(5-Fluoro-1H-benzoimidazol-2-yl)-2,2-dimethyl-propyl]-carbamic acid benzyl ester A solution of the mixture of 1 and 2 (2.24 g, 6.45 mmol) in glacial acetic acid (25 ml) was heated to 65° C. for 12 hrs. Acetic acid was removed under reduced pressure. The resulting salt was partitioned between dichloromethane and 1M aq. Na₂CO₃. The organic layer was washed with brine, dried over anhydrous MgSO₄, filtered and the solvent was removed under reduced pressure. The resulting crude reaction mixture was purified by flash chromatography (hexane/ethyl acetate:3/1) to give the title compound (1.92 g, 84% yield). LRMS: +ve ion 356 [M+1], –ve ion 354 [M–1]; HPLC data: RT 5.13 min.

Step C: 1S-(6-Fluoro-1H-benzoimidazol-2-yl)-2,2-dimethyl-propylamine

To a cold (5° C.) solution of [1S-(5-fluoro-1H-benzoimidazol-2-yl)-2,2dimethyl-propyl]-carbamic acid benzyl ester (400 mg, 1.13 mmol) in acetic acid (10 ml) was added 48% HBr in H₂O (12 ml). The resulting reaction mixture was stirred for 4 hrs at room temperature. Solvent was then removed under reduced pressure. The crude salt was dissolved in ethyl acetate and washed with 1M aq. Na₂CO₃ and brine. The organic layer was dried over anhydrous MgSO₄, filtered and the solvent removed in vacuo to provide the title compound (230 mg, 92%). ¹H-NMR; δ (CDCl₃), 7.51–7.44 (1H, dd, J=8.73, 4.73 Hz), 7.28–7.21 (1H, m), 7.02–6.93 (1H, m), 4.05 (1H, s), 1.04 (9H, s).

Step D: 4-Benzyloxy-2R-cyclopentylmethyl-N-[1S-(6-fluoro-1H-benzoimidazol-2-yl)-2,2-dimethyl-propyl]4-formylamino-butyramide To a solution of the 4-benzyloxy-2R-cyclopentylmethyl-4-formylamino-butyric acid pentafluorophenyl ester (426 mg, 9.05 mmol) in dichloromethane (6 ml) was added 1S-(6-fluoro-1H-benzoimidazol-2-yl)-2,2-dimethyl-propylamine (from Step C) (220 mg, 1.00 mmol), followed by triethylamine (189 µl, 1.36 mmol). The resulting reaction mixture was stirred for 12 hrs at room temperature. The reaction mixture was diluted with dichloromethane and washed with water (20 ml), 1M aq. Na₂CO₃ and brine. The organic layer was dried over anhydrous MgSO₄, filtered and the solvent was removed in vacuo. The residual yellow solid was purified by flash chromatography (hexanes/ethyl acetate from 1:2 to 1:5) to provide the title compound (270 mg, 59%).

Step E: 2R-Cyclopentylmethyl-N-[1-(5-fluoro-1H-benzoimidazol-2-yl)-2,2-dimethyl-propyl]-3-(formyl-hydroxy-amino)-propionamide To a solution of 4-benzyloxy-2R-cyclopentylmethyl-N-[1S-(6-fluoro-1H-benzoimidazol-2-yl)-2,2-dimethyl-propyl]-4-formylamino-butyramide (113 mg, 2.22 mmol) in ethanol (100 ml), under a blanket of argon, was added 10% palladium on charcoal (10 mg). Hydrogen was bubbled through the suspension for 15 min and the reaction was stirred under an atmosphere of hydrogen for 15 min. The palladium catalyst was filtered off and the solvent was removed in vacuo to yield the title compound as a white foam (73 mg, 78%). ¹H-NMR; δ (CDCl₃), 8.41 (0.4H, br s), 7.94 (0.6H, br s), 7.60–7.09 (2H, m), 6.91 (1H, m), 6.43 (1H, m), 5.31 (0.5H, d), 5.16 (0.5H, d), 4.08 (0.5H, m), 3.93 (0.5H, m), 3.75 (0.5H, m), 3.58 (0.5H, m), 3.25 (0.5H, m), 3.02 (0.5H, m), 1.80–0.80 (11H, m), 1.02 (9H, s). HPLC data: RT 4.93 min.

The compounds of Examples 2–3 and 5–8 were prepared by analogy with Example 1 starting from the appropriate 1,2 diaminobenzene. The compound of Example 4 was prepared in a similar manner using 2R-[(benzoyloxy-formylamino)-methyl]-hexanoic acid in place of 4-benzyloxy-2R-cyclopentylmethyl-4-formylaminobutyric acid pentafluorophenyl ester.

EXAMPLE 2

N-[1-(5-Chloro-1H-benzoimidazol-2-yl)-2,2-dimethyl-propyl]-2-cyclopentylmethyl-3-(formyl-hydroxy-amino)-propionamide

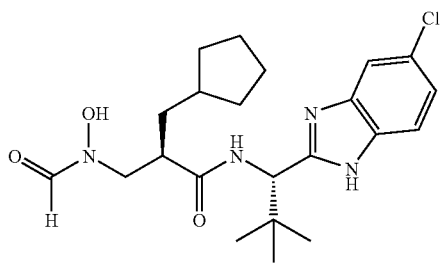

¹H-NMR; δ (CDCl₃), 8.44 (0.4H, s), 7.95 (0.6H, s), 7.71–7.48 (1H, m), 7.30–7.02 (2H, m), 5.30 (0.5H, d, J=9 Hz), 5.14 (0.5H, br s), 4.01–3.89 (1H, m), 3.80 (0.5H, d, J=12 Hz), 3.60 (0.5H, d, J=12 Hz), 3.23 (0.4H, br s), 3.01 (0.6H, br s) and 1.85–0.80 (20H, m). HPLC data: RT 4.84 min. LRMS: +ve ion 435 [M+1], −ve ion 433 [M−1].

EXAMPLE 3

N-[1-(1H-Benzoimidazol-2-yl)-2,2-dimethyl-propyl]-2-cyclopentylmethyl-3-(formyl-hydroxy-amino)-propionamide

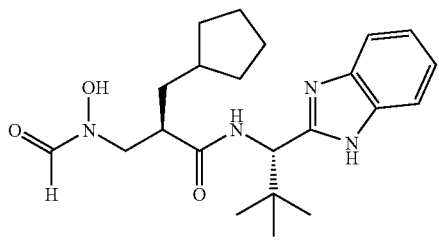

¹H-NMR; δ (CDCl₃), 8.43 (0.5H, br s), 7.95 (0.5H, br s), 7.68 (1H, br s), 7.48–7.10 (4H, m), 5.39 (0.5H, d, J=9.6 Hz), 5.26 (0.5H, d, J=8 Hz), 4.11 (0.5H, m), 3.98–3.94 (0.5H, dd, J=10.8, 13.3 Hz), 3.72 (0.5H, m), 3.59 (0.5H, d, J=11.8 Hz), 3.26 (0.5H, br s), 3.04 (0.5H, br s) and 1.73–0.81 (20H, m). HPLC data: RT 4.42 min.

EXAMPLE 4

2-[(Formyl-hydroxy-amino)-methyl]-hexanoic acid [1-(1H-benzoimidazol-2-yl)-2,2-dimethyl-propyl]-amide

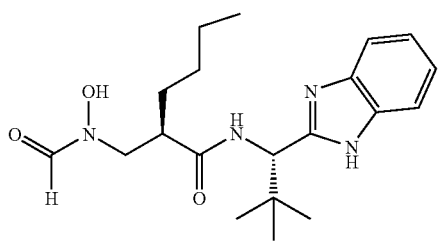

¹H-NMR; δ (CD₃OD), 8.28 (0.3H, s), 7.85 (0.7H, s), 7.54 (2H, br s), 7.22 (2H, dd, J=6.1, 3.1 Hz), 5.09 (0.7H, s), 5.07 (0.3H, s), 3.84–3.78 (0.3H, m), 3.79 (0.7H, dd, J=14.2, 9.5 Hz), 3.63 (0.3H, dd, J=14.0, 5.5 Hz), 3.44 (0.7H, dd, J=14.2, 4.6 Hz), 3.17–2.97 (0.7H, m), 2.88–2.82 (0.3H, m), 1.58–1.35 (2H, m), 1.23–1.02 (4H, m), 1.04 (2.7H, s), 1.02 (6.3H, s), 0.65 (0.9H, t, J=6.8 Hz) and 0.63 (2.1 H, t, J=7.1 Hz).

EXAMPLE 5

2R-Cyclopentylmethyl-N-[2,2-dimethyl-1S-(1H-naphtho[2,3-d]imidazol-2-yl)-propyl]-3-(formyl-hydroxy-amino)-propionamide

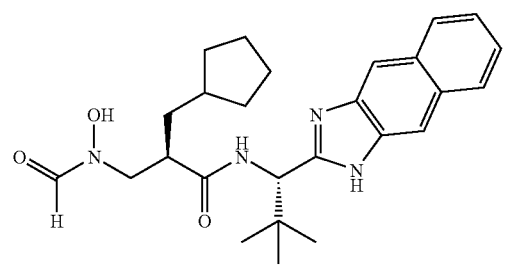

¹H-NMR; δ (DMSO), 10.06 (0.4 H, s), 9.53 (0.6H, s), 8.30 (1.3H, m), 8.12 (1H, s), 7.97 (2H, d, J=9.3 Hz), 7.94 (1H, s), 7.81 (0.7H, s), 7.35 (2H, br s), 5.10 (1H, m), 3.63 (1H, m), 3.47 (0.6H, m), 3.32 (0.4H, m), 2.94 (1H, m), 1.67 (1H, m), 1.36 (2H, m), 1.08 (2H, m) 0.99 (9H, s) and 0.87 (2H, m). ¹³C-NMR; δ (DMSO), 173.4, 158.7, 158.5, 144.1, 134.7, 130.2, 129.7, 128.3, 127.7, 123.9, 123.2, 115.1, 106.8, 56.1, 52.5, 49.1, 43.2, 43.0, 37.9, 37.7, 36.1, 35.5, 32.6, 32.4, 32.3, 27.0 and 24.7. LCMS: +ve ion 451 [M+H], for major peak. HPLC: RT=3.54 min.

EXAMPLE 6

2R-Cyclopentylmethyl-N-[2,2-dimethyl-1S-(5-methyl-1H-benzoimidazol-2-yl)-propyl]-3-(formyl-hydroxy-amino)-propionamide

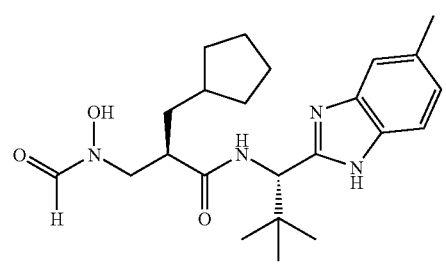

¹H-NMR; δ (CH₃OD), 8.29 (0.3H, s), 7.85 (0.7H, s), 7.41 (1H, d, J=8.1 Hz), 7.32 (1H, s), 7.05 (1H, d, J=8.2 Hz), 5.08 (1H, m), 3.80 (1H, m), 3.62 (0.3H, m), 3.44 (0.7H, m), 3.05 (0.7H, m), 2.91 (0.3H, m), 2.44 (3H, s), 1.41 (9H, m), 1.04 (3H, s), 1.01 (6H, s), 0.93 (2H, m). ¹³C-NMR; δ (CH₃OD), 176.5, 176.2, 164.4, 159.7, 154.5, 154.3, 133.9, 125.5, 73.0, 70.3, 65.1, 58.4, 58.3, 54.3, 50.7, 45.9, 45.8, 39.6, 37.9, 37.8, 37.6, 37.1, 36.8, 34.2, 34.1, 34.0, 27.5, 26.3 and 22.1. LRMS: +ve ion 415 [M+H], 437 [M+Na]. HPLC: RT=5.16 min

EXAMPLE 7

2R-Cyclopentylmethyl-3-(formyl-hydroxy-amino)-N-[1S-(4-hydroxy-1H-benzoimidazol-2-yl)-2,2-dimethyl-propyl]-propionamide

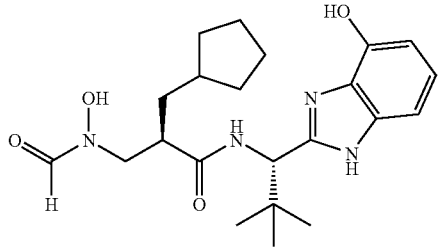

¹H-NMR; δ (CH₃OD), 8.28 (0.4H, s), 7.84 (0.6H, s), 7.01 (2H, m), 6.61 (1H, m), 5.09 (1H, m), 3.80 (1H, m), 3.62 (0.3H, m), 3.45 (0.7H, m), 2.87 (0.3H, m), 1.73 (1H, m), 1.38 (8H, m), 1.03 (3H, s), 1.01 (6H, s), 0.93 (2H, m). ¹³C-NMR; δ (CH₃OD), 176.4, 176.2, 164.3, 159.6, 153.2, 124.7, 108.4, 58.1, 54.3, 50.7, 46.0, 45.9, 39.7, 39.6, 37.9, 36.9, 34.1, 34.0, 27.5, 26.2 and 26.1. LRMS: +ve ion 417 [M+H], 439 [M+Na]. HPLC: RT=4.62 min.

EXAMPLE 8

N-[1S-(5-Cyano-1H-benzoimidazol-2-yl)-2,2-dimethyl-propyl]-2R-cyclopentylmethyl-3-(formyl-hydroxy-amino)-propionamide

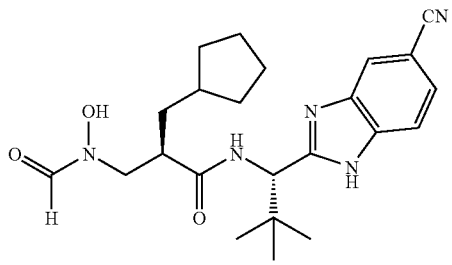

¹H-NMR; δ (CH₃OD), 8.29 (0.4H, s), 7.96 (1H, s), 7.86 (1H, d, J=8.3 Hz), 7.54 (1H, d, J=8.3 Hz), 5.11 (1H, m), 3.80 (1H, m), 3.61 (0.4H, m), 3.46 (0.6H, m), 3.10 (0.6H, m), 2.90 (0.4H, m), 1.41 (11H, m), 1.06 (3H, s) and 1.04 (6H, s). ¹³C-NMR; δ (CH₃OD), 176.8, 176.5, 164.4, 159.7, 158.7, 158.5, 127.4, 121.1, 106.7, 58.7, 58.4, 54.2, 50.7, 48.0, 45.6, 39.6, 37.9, 37.8, 36.6, 35.2, 34.5, 34.1, 34.0, 27.7, 27.4, 26.5, 26.2 and 18.8. LRMS: +ve ion 426 [M+H], −ve ion 424 [M−H]. HPLC: RT=5.29 min.

Examples 9 & 10 were prepared by analogy with Example 1 using glycine in place of t-leucine.

EXAMPLE 9

N-(1H-Benzoimidazol-2-ylmethyl)-2R-cyclopentylmethyl-3-(formyl-hydroxy-amino)-propionamide

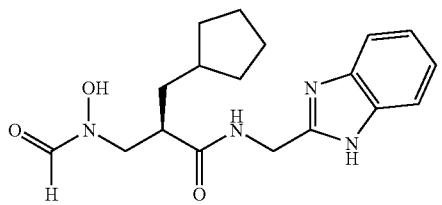

¹H-NMR; δ (CH₃OD), 8.32 (0.5 H, s), 7.89 (0.5H, s), 7.54 (2H, m), 7.22 (2H, m), 4.85 (1H, m), 4.42 (1H, m), 3.96 (0.1H, dd, J=13.9 4.3 Hz), 3.83 (0.4H, dd, J=13.8, 4.8 Hz), 3.69 (1H, m), 3.56 (0.5H, dd, J=14.1, 4.8 Hz), 2.93 (0.5H, m), 2.80 (0.5H, m), 1.61 (9H, m) and 1.11 (2H, m). ¹³C-NMR; δ (CH₃OD), 177.5, 177.0, 164.6, 160.4, 153.7, 153.3, 124.1, 116.3, 116.1, 54.2, 53.8, 51.8, 46.5, 46.2, 46.0, 39.7, 39.6, 38.6, 38.3, 38.2, 37.7, 37.5, 34.4, 33.9, 33.8, 26.4 and 20.9. LRMS: +ve ion 345 [M+H], 367 [M+Na]. HPLC: RT=4.72 min.

EXAMPLE 10

2R-Cyclopentylmethyl-3-(formyl-hydroxy-amino)-N-(5-methyl-1H-benzoimidazol-2-ylmethyl)-propionamide

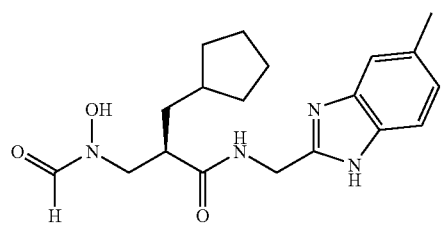

¹H-NMR; δ (CH₃OD), 8.31 (0.5H, s), 7.89 (0.5H, s), 7.36 (2H, m), 7.04 (1H, d, J=7.9 Hz), 4.80 (1H, m), 4.39 (1H, m), 3.69 (2H, m), 2.92 (0.5H, m), 2.80 (0.5H, m), 2.43 (3H, s), 1.60 (9H, m) and 1.13 (2H, m). ¹³C-NMR; δ (CH₃OD), 177.4, 164.6, 153.3, 125.5, 54.1, 51.8, 46.2, 46.0, 39.6, 38.5, 38.3, 37.7, 34.5, 34.4, 33.9, 33.8, 26.4 and 22.0. LRMS: +ve ion 359 [M+H], −ve ion 357 [M−1].

EXAMPLE 11

2R-Cyclopentylmethyl-3-(formyl-hydroxy-amino)-N-(1-methyl-1H-benzoimidazol-2-ylmethyl)-propionamide

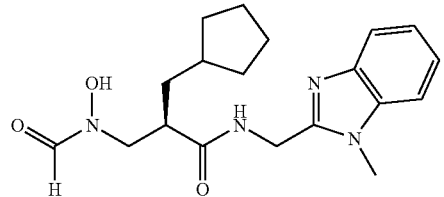

Example 11 was prepared in a similar manner to Example 1 using glycine in the place of t-leucine. The N-methyl substituent was introduced on to the benzimidazole nitrogen using the procedure detailed below.

2R-Cyclopentylmethyl-3-(formyl-hydroxy-amino)-N-(1-methyl-1H-benzoimidazol-2-ylmethyl)-propionamide To a solution of N-(1H-Benzoimidazol-2-ylmethyl)-2R-cyclopentylmethyl-3-(formyl-hydroxy-amino)-propionamide (80 mg, 0.23 mmol) in anhydrous THF (7 ml) was added triethylamine (30 µl, 0.22 mmol) and iodomethane (14 µl, 0.22 mmol). The reaction was stirred at 30° C. for approx. 3.5 hours. The material had not fully dissolved, so DMF was added and the reaction stirred for a further 2 hours at 30° C. LRMS analysis showed presence of starting material, more triethylamine (30 µl, 0.22 mmol) and iodomethane (14 μl, 0.22 mmol) were added and the reaction stirred at 30° C. over night. The solvent was removed in vacuo and the residue was dissolved in DCM, washed with water, dried over anhydrous magnesium sulfate and filtered. The solvent was removed in vacuo and the crude mixture was purified by preparative HPLC to obtain the title compound as a yellow oil. $^1$H-NMR; δ (CH$_3$OD), 8.31 (0.4H, s), 7.87 (0.6H, s), 7.58 (2H, m), 7.26 (2H, m), 4.89 (1H, m), 4.55 (1H, m), 3.82 (1.2H, s), 3.81 (1.8H, s), 3.66 (2H, m), 2.93 (0.4H, m), 2.82 (0.6H, m), 1.63 (9H, m) and 1.09 (2H, m). $^{13}$C-NMR; δ (CH$_3$OD), 177.2, 176.7, 164.6, 166.2, 130.6, 130.2, 128.2, 124.6, 124.1, 124.0, 123.9, 120.0, 119.4, 111.4, 54.1, 51.7, 46.1, 45.9, 39.6, 38.8, 38.4, 37.9, 37.6, 37.2, 34.4, 33.9, 30.8, 30.6 and 26.4. LRMS: +ve ion 359 [M+H], 381 [M+Na]. HPLC: RT=4.81 min.

EXAMPLE 12

3-Cyclopentyl-2R-[(formyl-hydroxy-amino)-methyl]-N-[1S-(1H-imidazol-2-yl)-2,2-dimethyl-propyl]-propionamide

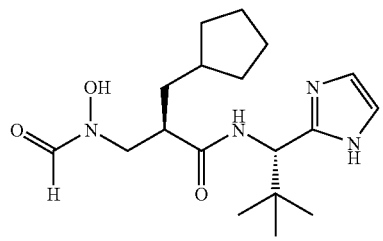

$^1$H-NMR; δ (CDCl$_3$), 8.33 (0.6 H, s), 7.86 (0.4H, s), 7.81 (0.4H, s), 7.14 (0.6H, s), 6.90 (2H, m), 5.15 (0.4H, d, J=9.6 Hz), 5.06 (0.6H, d, J=8.6 Hz), 4.00 (0.6H, m), 3.88 (0.4H, m), 3.65 (0.6H, m), 3.47 (0.4H, m), 3.19 (0.4H, m), 2.98 (0.6H, m), 1.56 (9H, m), 0.96 (6H, m), 0.95 (2H, m) and 0.77 (3H, s). LRMS: +ve ion 351 [M+H], –ve ion 349 [M–H]. HPLC: RT=3.37 min.

The title compound was prepared from 2R-[(Benzyloxyformylamino)-methyl]-hexanoic acid and 1S-(1H-Imidazol-2-yl)-2,2-dimethyl-propylamine by analogy with Example 1. The preparation of 1S-(1H-Imidazol-2-yl)-2,2-dimethyl-propylamine is detailed below (see Scheme 2)

Scheme 2

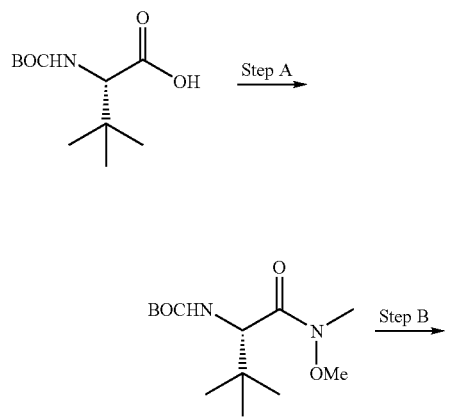

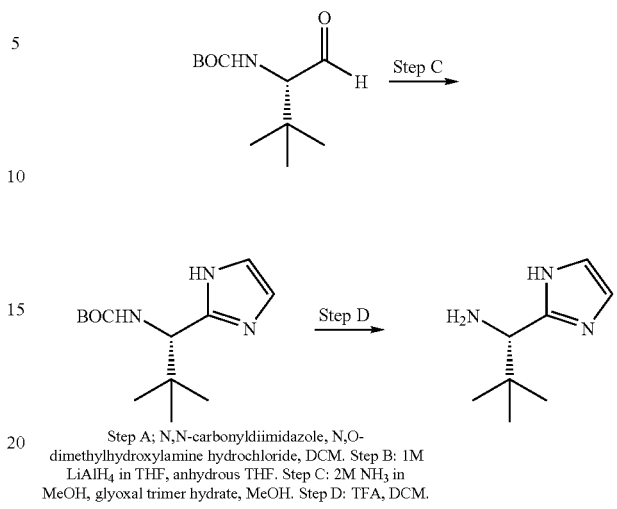

Step A; N,N-carbonyldiimidazole, N,O-dimethylhydroxylamine hydrochloride, DCM. Step B: 1M LiAlH$_4$ in THF, anhydrous THF. Step C: 2M NH$_3$ in MeOH, glyoxal trimer hydrate, MeOH. Step D: TFA, DCM.

Step A: [1S-(Methoxy-methyl-carbamoyl)-2,2-dimethyl-propyl]-carbamic acid tert-butyl ester To a solution of BOC protected t-leucine (30 g, 0.13 mol) in DCM (400 ml) was added N,N-carbonyldiimidazole (63.3 g, 0.39 mol) portionwise. Evolution of CO$_2$ gas was observed and the reaction allowed to stir for approx. 15 minutes before addition of N,O-dimethylhydroxylamine hydrochloride (38 g, 0.39 mol). The reaction was stirred overnight at ambient temperature. The solvent was removed in vacuo and the residue dissolved in ethyl acetate, washed with 1M hydrochloric acid, saturated sodium carbonate solution and saturated sodium chloride solution, dried over anhydrous magnesium sulfate and filtered. The solvent was removed in vacuo to obtain a clear oil (26.5 g) that was purified by flash chromatography (30% ethyl acetate/hexanes) when required.

$^1$H-NMR; δ (CH$_3$OD) 5.20 (1H, br s), 4.67 (1H, d, J=9.5 Hz), 3.79 (3H, s), 3.20 (3H, s), 1.44 (9H, s) and 0.99 (9H, s).

Step B: (1S-Formyl-2,2-dimethyl-propyl)-carbamic acid tert-butyl ester

To a stirred solution of [1S-(Methoxy-methyl-carbamoyl)-2,2-dimethyl-propyl]-carbamic acid tert-butyl ester (1.4 g, 5.11 mmol) in anhydrous THF (40 ml), under a blanket of argon and in a dry ice/acetone bath, was added lithium aluminium hydride. The reaction was stirred in the cooling bath for approx. 1 hour, then allowed to warm to room temperature and stir overnight. The reaction was cooled in an ice/water bath before addition of ethyl acetate (4 ml), water (0.2 ml), 2.5M sodium hydroxide (0.31 ml) and water (0.5 ml). The reaction mixture was allowed to warm to room temperature and stir for approx. 45 minutes. The resulting semi-soild was filtered off, washed with ethyl acetate and the filtrate concentrated in vacuo to obtain a pale yellow oil (1.02 g, 92%). $^1$H-NMR; δ (CDCl$_3$) 9.84 (1H, s), 5.15 (1H, br s), 4.15 (1H, br s), 1.44 (9H, s) and 1.04 (9H, s).

Step C: [1S-(1H-Imidazol-2-yl)-2,2-dimethyl-propyl]-carbamic acid tert-butyl ester To a stirred solution of (1S-Formyl-2,2-dimethyl-propyl)-carbamic acid tert-butyl ester (1.02 g, 4.75 mmol) in methanol (6 ml), was added 2M $NH_3$ in MeOH (11 ml, 21.8 mmol) and glyoxal trimer hydrate (499 mg, 2.37 mmol). The reaction was stirred at room temperature overnight, then diluted with water and extracted with ethyl acetate. The organic layer was washed with saturated sodium chloride solution, dried over anydrous magnesium sulfate and filtered. The solvent was removed in vacuo to obtain a yellow oil (879 mg) that was purified by flash chromatography (3–4% methanol/DCM) to yield a white solid (495 mg, 95%). LRMS: +ve ion 254 [M+H], −ve ion 252 [M−1]. $^1$H-NMR; δ ($CDCl_3$) 6.92 (2H, s), 5.70 (1H, d, J=9.8 Hz), 4.65 (1H, d, J=9.7 Hz), 1.42 (9H, s) and 0.99 (9H, s).

Step D: 1S-(1H-Imidazol-2-yl)-2,2-dimethyl-propylamine

To a solution of [1S-(1H-Imidazol-2-yl)-2,2-dimethyl-propyl]-carbamic acid tert-butyl ester (495 mg, 1.95 mmol) in DCM (10 ml), was added TFA (10 ml). The reaction was stirred at room temperature for approx. 4 hours. The solvent was removed in vacuo and the TFA co-evaporated with toluene. The residue was dissolved in methanol and Amberlyst A-21 ion exchange resin was added until pH 8 was obtained. The resin was filtered off and the solvent removed in vacuo to obtain the title compound as an oil (276 mg, 93%). LRMS: +ve ion 154 [M+H]. $^1$H-NMR; δ ($CH_3OD$) 7.01 (2H, s), 3.85 (1H, s) and 0.96 (9H, s).

Biological Example

The susceptibilities of two strains of bacteria to the compounds of Example 1–4 were determined by a standard agar plate dilution method following recommendations in British Society for Antimicrobial Chemotherapy Working Party. 1991, "A guide to sensitivity testing British Society for Antimicrobial Chemotherapy, London, United Kingdom". Briefly, Iso-Sensitest agar (pH 7.2: Oxoid, United Kingdom) is employed, supplemented with 5% horse blood (Oxoid) and 20 μg of NAD (Sigma) per ml are added to support growth of fastidious bacteria. The inoculum used is approximately $10^4$ colony forming units of each isolate contained in a volume of 1 μl. Plates are incubated 18 to 24 hr in air, or for fasidious bacteria an atmosphere enriched with 4–6% carbon dioxide at 35° C. The MIC is determined as the lowest concentration of an antimicrobial tested that inhibited growth of the inoculum, disregarding a single persisting colony or faint haze caused by the inoculation. The results were as follows:

| Example No | S. aureus ATCC 29213 MIC μg/ml | S. pneumoniae ATCC 49619 MIC μg/ml |
|---|---|---|
| 1 | 4 | 2 |
| 2 | 8 | 2 |
| 3 | 8 | 2 |
| 4 | 8 | 4 |

The invention claimed is:
1. A compound of formula (I) or a pharmaceutical or veterinarily acceptable salt, hydrate or solvate thereof:

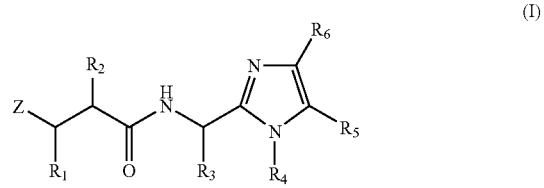

wherein:
Z represents a radical of formula —N(OH)CH(=O);
$R_1$ represents hydrogen, methyl or trifluoromethyl;
$R_2$ represents methyl, ethyl, n-or iso-propyl, n- and iso-butyl, n-pentyl, iso-pentyl, 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl;
$R_3$ represents hydrogen, methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxethyl, 2-carboxyethyl, 2-methylcarbamoylethyl, 2-carbamoylethyl, or 4-aminobutyl; and
$R_4$ represents hydrogen, or methyl; and
(a) $R_5$ and $R_6$ independently represent:
hydrogen, halogen, trifluoromethyl, or $(C_1–C_6)$alkyl, $(C_2–C_6)$alkenyl, $(C_2–C_6)$alkynyl, aryl, heterocyclyl, aryl$(C_1–C_6)$alkyl-, or heterocyclyl$(C_1–C_6)$alkyl-, any of which may be optionally substituted by
$(C_1–C_6)$alkyl, halogen, trifluoromethyl, cyano, nitro, oxo, phenoxy or phenylthio-, —$OR^A$, —$SR^A$, —$NHR^A$, —$NR^AR^B$, —NH-$COR^A$, —$CONHR^A$, —$CONR^AR^B$, or —$COOR^A$, wherein
$R^A$ and $R^B$ are independently hydrogen or $(C_1–C_4)$alkyl,
or in the case where $R^A$ and $R^B$ are attached to a nitrogen atom then $R^A$ and $R^B$ taken together with the nitrogen atom to which they are attached form a monocyclic 5–7 membered ring; or
(b) $R_5$ and $R_6$ taken together with the carbon atoms to which they are attached form a fused monocyclic or bicyclic carbocyclic ring which may be further substituted with any of the substituent groups listed under (a).

2. The compound of claim 1 wherein $R_1$ is hydrogen.

3. The compound as claimed in claim 1 wherein $R_2$ is n-propyl, n-butyl, n-pentyl, or cyclopentylmethyl.

4. The compound as claimed in claim 1 wherein $R_3$ is tert-butyl.

5. The compound as claimed in claim 1 wherein $R_4$ is hydrogen.

6. The compound as claimed in claim 1 wherein $R_5$ and $R_6$ are independently hydrogen, methyl, trifluoromethyl, phenyl, bromo, chloro, fluoro, methoxy, hydroxymethyl, dimethylaminomethyl-, ethoxymethyl-, 4-methylpiperazine-1-carbonyl-, 4-methyl-piperazin-1-ylmethyl-, morpholin-4-ylmethyl-, methoxycarbonyl, thiazol-2-yl-, phenoxymethyl-, pyrrolidin-1-ylmethyl-, piperidin-1-ylmethyl-, —C(O)NH$_2$, (CH$_2$)$_2$CO$_2$CH$_3$, —CH(OH)CH(CH$_3$)$_2$, CH(OH)CH$_3$, or —CH(OH)Ph; or wherein $R_5$ and $R_6$ taken together with the carbon atoms to which they are attached form a fused benzo ring which may be substituted.

7. The compound as claimed in claim 1 wherein $R_1$ is hydrogen, $R_2$ is n-propyl, n-butyl, n-pentyl, or cyclopentylmethyl, $R_3$ is tert-butyl, and $R_4$ is hydrogen.

8. A pharmaceutical composition comprising a compound as claimed in claim 1 together with a pharmaceutical acceptable carrier.

* * * * *